United States Patent
De Ferra et al.

(10) Patent No.: US 10,869,843 B2
(45) Date of Patent: Dec. 22, 2020

(54) METHOD FOR INCREASING MUSCLE MASS AND STRENGTH

(75) Inventors: Lorenzo De Ferra, Patrica (IT);
Marvin Heuer, Orlando, FL (US);
Scott Hagerman, St. Paul, MN (US);
Martin Purpura, Milwaukee, WI (US);
Ralf Jager, Milwaukee, WI (US)

(73) Assignee: CHEMI NUTRA, White Bear Lake, MN (US)

( * ) Notice: Subject to any disclaimer, the term of this patent is extended or adjusted under 35 U.S.C. 154(b) by 174 days.

(21) Appl. No.: 13/373,649

(22) Filed: Nov. 23, 2011

(65) Prior Publication Data

US 2012/0141448 A1 Jun. 7, 2012

Related U.S. Application Data

(60) Provisional application No. 61/458,400, filed on Nov. 23, 2010.

(51) Int. Cl.
| | | |
|---|---|---|
| A61K 31/661 | (2006.01) | |
| A61K 31/122 | (2006.01) | |
| A61K 38/27 | (2006.01) | |
| A61K 31/685 | (2006.01) | |
| A61K 33/06 | (2006.01) | |
| A61K 33/24 | (2019.01) | |
| A61K 38/28 | (2006.01) | |
| A61K 31/198 | (2006.01) | |
| A61K 45/06 | (2006.01) | |
| A61K 38/30 | (2006.01) | |
| A61K 38/01 | (2006.01) | |
| A61K 35/20 | (2006.01) | |
| A61K 38/17 | (2006.01) | |

(52) U.S. Cl.
CPC .......... *A61K 31/122* (2013.01); *A61K 31/198* (2013.01); *A61K 31/661* (2013.01); *A61K 31/685* (2013.01); *A61K 33/06* (2013.01); *A61K 33/24* (2013.01); *A61K 35/20* (2013.01); *A61K 38/014* (2013.01); *A61K 38/1709* (2013.01); *A61K 38/27* (2013.01); *A61K 38/28* (2013.01); *A61K 38/30* (2013.01); *A61K 45/06* (2013.01)

(58) Field of Classification Search
CPC ........................... A61K 31/122; A61K 31/198
USPC .................................................. 424/94.1, 646
See application file for complete search history.

(56) References Cited

U.S. PATENT DOCUMENTS

| | | | |
|---|---|---|---|
| 6,103,764 A | 8/2000 | Nissen | |
| 6,525,027 B2 | 2/2003 | Vazquez et al. | |
| 7,749,547 B2 | 7/2010 | Heuer et al. | |
| 7,790,688 B2 | 9/2010 | Wolfe et al. | |
| 8,124,594 B2 | 2/2012 | Purpura et al. | |
| 2003/0113390 A1* | 6/2003 | Hoie ........................ | A23L 1/30 424/757 |
| 2004/0166181 A1* | 8/2004 | Hegenauer ............. | A61K 36/11 424/757 |
| 2005/0008678 A1* | 1/2005 | Howard et al. ................ | 424/439 |
| 2007/0015686 A1* | 1/2007 | Heuer ....................... | A23L 2/52 424/729 |
| 2008/0095865 A1 | 4/2008 | Heuer et al. | |
| 2009/0142410 A1 | 6/2009 | Heuer et al. | |
| 2009/0143339 A1 | 6/2009 | Purpura et al. | |
| 2012/0141448 A1 | 6/2012 | De Ferra et al. | |

FOREIGN PATENT DOCUMENTS

| | | |
|---|---|---|
| CN | 1200274 | 12/1998 |
| CN | 101455655 A | 6/2009 |
| DE | 102007030495 A1 | 1/2009 |
| EP | 1214928 | 6/2002 |
| EP | 0904087 | 9/2002 |
| EP | 0999846 | 1/2004 |
| RU | 2292732 C2 | 2/2007 |
| WO | 9520967 | 8/1995 |
| WO | WO 99/49741 | * 10/1999 |
| WO | 2005044176 | 5/2005 |
| WO | 2013175386 | 11/2013 |

OTHER PUBLICATIONS

Ivy, Nutrient Timing, The Future of Sports Nutrition, p. 1-110, 2004.*
Lehman et al., FASEB Journal, vol. 21, p. 1075-1087, 2007.*
Lieber et al., Hepatology, vol. 12, No. 6, p. 1390-1398, 1990.*
Vandenberghe et al. (Journal of Applied Physiology, vol. 83, No. 6, p. 2055-2064, 1985).*
Hoffman et al. (Journal of Sports Science and Medicine, vol. 3, p. 118-130, 2004).*
American Lecithin Company, "About Soy Phospholipids", Feb. 20, 2001, accessed Jan. 22, 2013.*
Wikipedia, http://en.wikipedia.org/wiki/Complete_protein, accessed Jul. 26, 2016.*

(Continued)

*Primary Examiner* — Erin M. Bowers

(74) *Attorney, Agent, or Firm* — Silvia Salvadori, P.C.; Silvia Salvadori

(57) ABSTRACT

Phosphatidic acid is administered orally to increase muscle mass and strength in exercising mammals. Phosphatidic acid is administered orally to aging, bedridden or cachectic patients to improve nitrogen balance. The preferred form of phosphatidic acid for administration is phosphatidic acid-enriched lecithin. Creatine is co-administered orally to increase the muscle-building and strength effect. Other suggested additives include nutritional and herbal supplements, micronutrients and hormones.

4 Claims, No Drawings

(56) References Cited

OTHER PUBLICATIONS

Gibala, https://www.iahsaa.org/Sports_Medicine_Wellness/Nutrition/GSSI-Protein_and_Endurance.pdf, 2006, accessed Apr. 3, 2017.*
Anderson et al., J. Nutr. 134(4): 9745-9795 (2004).*
Wikipedia, https://en.wikipedia.org/wiki/Collagen, accessed Apr. 3, 2017.*
Metcalfe et al., Food Allergy: Adverse Reactions to Foods and Food Additives, 4th Edition, "Appendix: Allergen Avoidance Handouts", pp. 596-599, 2008.*
Zanchi et al., Eur. J. Appl. Physiol. 102: 253-263 (2008).*
Cobb et al., Lecithin Supplementation in Healthy Volunteers—Effect on Cholesterol Esterification and Plasma and Bile lipids, Nutr. Metab. vol. 24, 1980, pp. 228-237.
Foster, Regulation of mTOR by Phosphatidic Acid?, Cancer Research vol. 67:(1), pp. 1-4, 2007.
Greenhaff et al., Effect of oral creatine supplementation on skeletal muscle phosphocreatine resynthesis, Amer. J. Physiol. 266 (5Pt 1), 1994, pp. E725-E730.
Hornberger, et al., The Role of Phospholipase D and Phosphatidic Acid in the Mechanical Activation of mTOR Signaling in Skeletal Muscle, PNAS, vol. 103, No. 12, Mar. 2006, pp. 4743-4746.
Jäger et al, Phospholipids and sports performance, J. Internat. Soc. of Sports Nutrition, 4:5, 2007, 8 pgs.
Kimball, The role of nutrition in stimulating muscle protein accretion at the molecular level, Biochem. Soc. Trans. 35, part 5, 2007, pp. 1298-1301.
Lehman et al., Phospholipase D2-derived phosphatidic acid binds to and activates ribosomal p70 S6 kinase independently of mTOR, FASEB J. vol. 21, pp. 1075-1087, 2007.
Veverka et al., Structural characterization of the interaction of mTOR with phosphatidic acid and a novel class of inhibitor: compelling evidence for a central role of the FRB domain in small molecule-mediated regulation of mTOR, Oncogene (2008) 27, 585-595.
Vukovich et al., Body Composition in 70-Year-Old Adults Responds to Dietary beta-Hydroxy-beta-Methylbutyrate Similarly to That of Young Adults, 2001 Am. Soc. Nutr. Sci. 2049-2053.
Xu et al., Activation of mTOR signaling by novel fluoromethylene phosphonate analogues of phosphatidic acid, Biorg. & Med. Chem. Lett. 14 (2004) 1461-1464.
Zanchi et al, Mechanical stimuli of skeletal muscle: implications on mTOR/p70s6k and protein synthesis, Eur J Appl Physiol (2008) 102:253-263.
Walker et al., Exercise, Amino Acids, and Aging in the Control of Human Muscle Protein Synthesis, Medicine & Science in Sports & Exercise, 2011, pp. 2249-2258.
Sengupta et al., Regulation of the mTOR Complex 1 Pathway by Nutrients, Growth Factors, and Stress, Molecular Cell vol. 40, Oct. 2010, pp. 310-322.
Hornberger et al., Regulation of mTOR by Mechanically Induced Signaling Events in Skeletal Muscle, Cell Cycle 5:13, Jul. 2006, pp. 1391-1396.
Harrington et al., Restraining PI3K: mTOR signalling goes back to the membrane, TRENDS in Biochemical Sciences, vol. 30, No. 1, Jan. 2005, pp. 35-42.

Jkwok, "Chemi Nutra Files Phosphatidic Acid Patent for Muscle Mass, Strength," Nutritional Outlook (2012): 1-3 (XP-002680716).
International Search Report for related international application No. PCT/IB2012/052543 dated Apr. 9, 2012.
Written opinion for related international application No. PCT/IB2012/052543 dated Apr. 9, 2012.
Hagerman, "News release—Chemi Nutra Files Patent for Phosphatidic Acids's (PA) Ability to Increase Muscle Mass and Strength," Chemi Nutra (2012) XP002680715. <<http://www.cheminutra.com/news/Press_Release_Chemi_Nutra_Files_Patent.pdf>> retrieved on Jul. 25, 2012.
Jager et al.. "Phospholipids and sports performance." Journal of the International Society of Sports Nutrition. Biomed Central LTD. LO (Jul. 25, 2007) 4 (1): 5. 8 pp.
O'Neil et al., "The role of phosphoinositide 3-kinase and phosphatidic acid in the regulation of mammalian target of rapamycin following eccentric contractions," J Physiol 587.14 (2009) 3691-3701.
Winter et al., "Phosphatidic acid mediates activation of mTORC1 through the ERK signaling pathway," Am J Physiol Cell Physiol (Apr. 28, 2010) 299: C335-C344; 001: 10.1152/ajpcell.00039.2010.
Foster, "Phosphatidic acid and lipid-sensing by mTOR," Trends in Endocrinology and Metabolism (2012) 1-7.
Fukami et al., "Phosphatidic Acid That Accumulates in Platelet-derived Growth Factor-stimulated Balb/c 3T3 Cells Is a Potential Mitogenic Signal," Journal of Biological Chemistry (Jun. 5, 1991) 267 (16): 10988-10993, 1992.
Minetti et al.. "G {alpha} i2 Signaling Promotes Skeletal Muscle Hypertrophy. Myoblast Differentiation. and Muscle Regeneration." Science Signaling (Nov. 29, 2011) 4 (201). raBO. (001: 10.1126/scisignal.200203B).14 pp.
Tanaka et al.. "Quantification of Phosphatidic Acid in Foodstuffs Using a Thin-Layer-Chromatography-Imaging Technique." J. Agric. Food Chem. (Apr. 4, 2012) 60: 4156-4161.
You et al.. "Mechanical Stimulation Induces mTOR Signaling via an ERK-Independent Mechanism: Implications for a Direct Activation of mTOR by Phosphatidic Acid." PLoS ONE (2012) 7 (10): e4725B. 001: 10.1371/journal. D pone.004725B. 12 pp.
International Search Report corresponding to PCT/US2013/042516 dated Jul. 17, 2013.
Written Opinion corresponding to PCT/US2013/042516 dated Jul. 17, 2013.
International Search Report corresponding to PCT/IB2013/054137 dated Oct. 24, 2013.
Written Opinion corresponding to PCT/IB2013/054137 dated Oct. 24, 2013.
Hoffman, J.R., et al., Efficacy of Phosphatidic Acid Ingestion on Lean . . . , Journal of the International Society of Sports Nutrition, 9:47, 2012.
Xuemin Wang, et al., Signaling Functions of Phosphatidic . . . , Progress in Lipid Research, 45, pp. 250-275, 2006.
Yimin Fang, et al., Phosphatidic Acid-Mediated Mitogenic Activation . . . , Science 294, 2001.
Science Signaling, Skeletal Muscle Atrophy Results in Loss of Strength, XP-002713142.
Tsaregorodtseva, et al., Feed Supplemental for Enhancement of Animal Muscle Mass, XP002680717, Aug. 20, 2006.

* cited by examiner

METHOD FOR INCREASING MUSCLE MASS AND STRENGTH

CROSS-REFERENCE TO RELATED APPLICATIONS

This application claims benefit of U.S. Provisional Patent Application, Ser. No. 61/458,400, filed Nov. 23, 2010, the entire teachings of which are herein incorporated by reference.

FIELD OF THE INVENTION

This invention relates to the administration of naturally occurring, isolated compounds which are biologically active in increasing muscle mass and strength.

BACKGROUND OF THE INVENTION

Muscles are the engines that move the body. Muscles are composed of the contractile proteins myosin and actin, which together form the myofibrils. Contraction occurs when actin ratchets over the myosin, shortening the length of myofibrils. Like all proteins, these contractile proteins begin with the genetic response, through the ribosomal synthetic apparatus. The resulting proteins are incorporated into existing myofibrils to increase the size of the muscle, called muscular hypertrophy, or to repair the damage that occurs during contraction. This system requires adequate nutrition to provide the amino acids that form the protein, but beyond that, the pathways are controlled by activating factors. Muscular hypertrophy, as is very well known, is achieved by exercise, especially exercise vigorous enough to reach the anaerobic threshold. Within a short time of commencing such exercise, a mammal will achieve measurable mass increase and strength. The increased demand has caused the synthetic machinery to be up regulated. The activating factors that may cause the upregulation in response to demand include the so-called "second messenger system" which is known to include phospholipases, protein kinases and others.

During growth, pregnancy and muscle development, the metabolism is in the anabolic phase, that is, more muscle is added than is broken down during the catabolic phase. Understanding the complexities of anabolism and catabolism and particularly, shifting the balance toward anabolism, is an ongoing and active research area.

The anabolic/catabolic balance is an important factor not only in healthy mammals during growth and development but also in disease and disease management. Muscle wasting in patients while at bed rest is a huge and common clinical issue. It is known that patients in intensive care units become catabolic, that is, tear down muscle tissue, almost immediately after confinement. It is also well known that astronauts become catabolic in weightless environment of space and begin losing muscle tissue and strength immediately in that environment. Even exercise in space is not completely sufficient to keep up with the muscle lost through catabolism. Significant loss of muscle has been shown even in healthy, young volunteers whose leg has been immobilized a cast for only two weeks (Hespel et al. J. Physiol. 536:625-633, 2001) Extreme loss of muscle tissue leads to a condition termed cachexia, which is often seen in cancer, trauma and burn patients.

A shift toward catabolism may occur as a normal part of aging and extraordinary measures are necessary to stave it off and shift the metabolism to a more anabolic state.

Athletes also can benefit from enhanced muscle development. In their training, especially in weight or cardiovascular training intense enough to reach the anaerobic threshold, they are constantly tearing down muscle fiber (catabolism) and rebuilding the fibers (anabolism). This cycle of rebuilding is especially rapid during the 90 minutes following exercise (the "anabolic window"). While the daily training itself increases muscle mass and strength, it is known that the addition of certain elements, vitamins and minerals to daily nutrition through supplementation will help increase muscle repair and growth.

Since protein is the main nitrogen-containing compound in the body and about 60%-70% of protein is found in muscle, a convenient measure of the anabolic/catabolic measure is nitrogen balance; the ratio between nitrogen ingested and nitrogen excreted. A positive nitrogen balance indicates growth and an increase in muscle; an equilibrium indicates a zero balance; while a negative nitrogen balance, if chronic, is an indication of bodily dysfunction which may lead to cachexia.

The need remains to discover a method and compositions to upregulate protein synthesis, in particular the synthesis of contractile proteins to improve the anabolic/catabolic ratio and nitrogen balance in both athletes and other persons.

SUMMARY OF THE INVENTION

This invention relates to the administration of a therapeutically effective amount of naturally occurring, isolated compounds which are biologically active in increasing muscle mass and strength by stimulation of anabolic metabolism. This invention relates specifically to the oral use of phosphatidic acid (PA) and particularly a novel PA from soy lecithin, termed PA-enriched lecithin, and more particularly to novel methods for administration of PA for the enhancement of muscle mass and/or strength in mammals such as humans, equines and canines. The methods of this invention are also directed to reverse the catabolism of muscle leading to sarcopenia in bedridden, aging or cachectic subjects or those in a weightless environment.

The shift in metabolism from the catabolic state to the anabolic state can be measured by determination of nitrogen balance, the ratio between nitrogen consumed as protein and nitrogen excretion as urea. Alternatively, the urinary excretion of creatinine may be followed.

The present application discloses oral administration of compositions having a therapeutically effective amount of PA or PA-enriched lecithin sufficient to affect intracellular and extracellular concentrations of PA in a mammal in order to shift the metabolism from the catabolic state to the anabolic state. This shift counteracts the decrease in muscle tissue occurring in normal aging and in extreme cases such as bed rest, cachexia and weightlessness. A further object of this invention is the improvement of exercise capacity in normal healthy mammals where increased muscle mass and strength is desired.

Lecithin is found in many natural products including but not limited to soybeans, peanuts, eggs, grains, liver, fish, legumes, safflower, milk. The exemplar lecithin described in this invention is soy lecithin. Lecithin from any source may be isolated to an essentially pure PA (at least 98% pure) by enzymatic conversion, a method well known in the art. However, a suitable composition is prepared from soy lecithin and contains at least 10%, more preferably 40-50% to 60% PA. This novel composition is termed PA-enriched lecithin. Minor components include 5-15% phosphatidyl choline, 1-5% lyso-phosphatidylcholine and 1-5% N-acyl phosphatidylethanolamine. These components neither increase nor interfere with the PA content and activity. Lecithin is meant to include chemically or enzymatically altered derivatives, such as DHA-soy lecithin.

For administration, a dosage of 0.1 grams to 40 grams of PA-enriched lecithin is administered to a mammal orally one to three times daily, preferably during the anabolic window, 90 minutes before to 90 minutes after exercise. When the mammal is a human, 0.5 to four grams is the recommended dosage. When the mammal is a horse, 10 to 40 grams is the recommended dosage. When the mammal is a whippet, 0.1 to 0.3 grams is the recommended dosage. When the mammal is a greyhound, 0.2 to 0.4 grams is the recommended dosage.

A gastric acid secretion inhibitory coating may be applied to the dose in a manner that protects the PA from degradation by gastric juices. Examples of such enteric coatings include polymers such as cellulose. Enteric coated PA can be incorporated in the manufacture of foods, drugs, and dietary supplements of complex formulations and various dosage forms including capsules, tablets, caplets, lozenges, liquids, solid foods, powders and other dosage forms that may be developed, without the need to impart enteric protection to the entire mixture, any other part of the mixture, or finished products.

Any methods of delivery and/or administration of PA is considered within the scope of this invention, including for example and not by way of limitation, tablet, capsule, powder, granule, microgranule, pellet, soft gel, controlled release form, liquid, solution, elixir, syrup, suspension, emulsion, magma, gel, cream ointment, lotion, transdermal, sublingual, ophthalmic, nasal, otic, aerosol, inhalation, spray, parenteral, suppository and the like. In suitable cases, PA may be administered by intravenous or intraarterial infusion. Compositions of the present invention may also be administered in nutraceutical or functional foods. In addition the effective amount of PA may be combined with amino acids, botanicals, functional foods, herbals, nucleotides, nutraceuticals, pharmaceuticals, proteins, and/or vitamins in an effort to enhance the targeted activity.

The administration of PA should be combined with as much exercise as the subject is able to perform, preferably within the anabolic window when the effect is more pronounced. This cycle of rebuilding actually starts approximately 90 minutes before exercise and is especially rapid and intense during the 90 minutes following exercise. An easily digested protein supplement such as whey protein increases the effect. Another recommended protein is partially hydrolyzed collagen. The protein should be taken from approximately 90 minutes before until 90 minutes after exercise for best effect.

An additional composition to increase muscle mass is a combination of creatine plus PA. Creatine is stored mainly in muscle tissue, where it is phosphorylated to creatine phosphate by ATP. The high energy phosphate bond of creatine phosphate is readily transferred to adenosine diphosphate by the enzyme creatine kinase forming ATP, which is available for muscle contraction and relaxation. Thus creatine phosphate may be considered a reservoir of muscle energy. Creatine is readily available in the market place; however about 30% of humans are creatine non-responders. In these subjects, no creatine is found in the tissues after creatine supplementation. PA has been found to switch creatine non-responders to creatine responders by a yet unknown mechanism. Creatine is generally administered at a dosage of about 3 to 20 grams.

DETAILED DESCRIPTION OF THE INVENTION

Lecithin is the commercial term for a naturally occurring mixture of phospholipids (also called phosphatides or phosphoglycerides). The "head" of a phospholipid is hydrophilic, while the hydrophobic "tails" are repelled by water and form aggregates. As a result of this configuration, phospholipids form natural barriers, segregating or insulating structures. The hydrophilic head contains the negatively charged phosphate group, and may contain other polar groups. The hydrophobic tail consists of long fatty acid hydrocarbon chains. The most common phospholipids are phosphatidic acid, phosphatidylethanolamine (PE), phosphatidylcholine (PC), phosphatidylserine (PS), and phosphatidylinositol (PI) Phospholipids occur widely throughout the plant and animal kingdoms. For example, the human spinal cord contains 6-10% and the human brain 4-6% (weight to weight, afterwards w/w) lecithin. Soybeans are the most important and economical source of commercial lecithin which has many applications in foods and industrial processes. It is to be understood that although the following examples use lecithin (1.48 to 3.08% w/w) and PA-enriched lecithin from soybeans (10 to 60% w/w), the scope of the claims attached cover lecithin, essentially pure PA and PA-enriched lecithin from any source, including but not limited to peanuts (1.11% w/w), calf liver (0.85% w/w), wheat (0.61% w/w), oatmeal (0.65% w/w), and eggs (0.39% w/w). Among refined substances, especially concentrated sources of lecithin include dehydrated egg yolk (14-20% w/w), natural egg yolk (7-10% w/w) wheat germ (2.82% w/w), soy oil (1.8% w/w) and butterfat (1.4% w/w).

Lecithin has been generally recognized as safe (GRAS) by the US FDA since 1979. Lecithin supplementation has been tested in numerous studies with healthy young athletes with no severe side effects (Jäger et al, 2007 J. Internat. Soc. of Sports Nutrition, 4:5)). Lecithin effects on lowering cholesterol levels (Cobb, 1980 Nutr. Metab. 24:228-237) has been studied. The daily consumption of lecithin in those studies, i.e., 22.5 grams per day for four weeks, contained from 0.4 to 0.7 grams of PA versus 1.6 grams of PA or PA-enriched lecithin per day for four to eight weeks, as is described in the study below. Interestingly, Cobb reports that no PA was found in plasma after 21 days of supplementation, verifying the ephemeral nature of PA metabolism. (Page 232Table III). At high lecithin levels, undesirable side effects of lecithin may include gastrointestinal distress, nausea and increased salivation.

The biological importance of phosphatidic acid is becoming recognized. PA is a common phospholipid and is a constituent of all cell membranes and administration has been suggested to improve membrane stability. However, the cell membrane portion is a minor component of the total phospholipid pool. PA is the smallest of the phospholipids on a molecular weight basis, but is important because it acts as a major precursor to the other phospholipids, all of which are crucial for membrane health. The further role of PA has been found to be as a key and crucial second messenger in muscular contraction, muscle cell growth and development. Although it is found in the food supply and is a natural component formed during digestion, its existence is ephemeral due to further degradation and entry into the phospholipid synthetic cycle. Before this invention, it has been unknown whether oral PA would raise systemic PA levels.

In addition to its structural role, PA is an important controller of protein synthesis. The pathways that regulate PA concentration in response to mechanical demand are as yet not fully defined, especially in the intact body. Under normal conditions, the concentration of PA depends on phospholipase D (PLD) enzyme activity, which causes the hydrolysis of phosphatidylcholine, a major membrane component, to PA and choline. PA then binds the FRB domain of the protein mTOR and activates p70S6K, which is one of the key ribosomes of the protein translation phase of protein synthesis. Blocking mTOR with the antibiotic rapamycin has been shown to block protein translation and stops the upregulation responding to mechanical stimulation and thereby the muscle growth.

In vitro studies with skeletal muscle stretch models, cell lysates or intact cell lines have pointed to PA's role in muscle metabolism. Signaling by the mammalian target of rapamycin (mTOR) is reported to be one aspect necessary for mechanical load-induced growth of skeletal muscle, muscular hypertrophy. The exact mechanisms for the mechanical activation of mTOR are not known, however, several studies indicate that both phospholipase D (PLD) and PA acting as a second messenger play crucial roles in the activation of mTOR signaling (See, for example, Hornberger, et al. Cell Cycle, Vol. 5, pp 1391-1396, 2006; Foster, Cancer Research Vol. 67, pp 1-4, 2007.)

The mechanism thus far worked out is as follows: PA binds to the FKBP12-rapamycin binding domain (FRB) of the protein mTOR and activates p70S6K, a ribosomal dual pathway signaling kinase, which is a key ribosome of the translation phase of protein synthesis. It has been shown that the PA role is critical to the synthesis of protein, particularly muscle proteins. In this in vitro study, an elevation in PA concentration was sufficient for the activation of mTOR signaling. Second, mechanical stimulation, such as in weight lifting-induced PLD activation, PA accumulation and mTOR signaling results in muscle growth. Finally, when PLD was blocked, PA did not accumulate and mTOR signaling was prevented.

Interestingly, further studies have indicated that PA binds to and activates p70S6K directly even in the absence of mTOR (Lehman et al. FASEB J. Vol. 21, pp. 1075-1087, 2007). This suggests that PA can have an anabolic potential at other times of the day regardless of whether mechanical activation takes place. This finding is of importance in the case of the cachectic, bedridden or elderly patient who is unable to perform sufficient exercise to induce mechanical activation.

Recent research has revealed that adenosine monophosphate-activated protein kinase (AMPK) can also inhibit mTOR signaling through the phosphorylation of TSC2, an upstream regulator of mTOR (Inoki et al. 2003 Genes Dev. 17: 1829-1834). PA has been shown to increase AMPK activity, which can result in inhibition of mTOR activity (Kimball 2007 Biochem. Soc. Trans. 35, part 5:1298-1301). Moreover, AMPK activation has been linked to the reduction of p70S6 kinase activity (Bolster et al. 2002; Kimura et al. 2003), therefore, because AMPK inhibits protein synthesis via a number of different pathways, it is likely that AMPK is a key regulator of cardiac hypertrophy. These results are contrary to the earlier findings and suggest that PA could actually decrease protein synthesis.

These in vitro studies can provide theoretical bases for the administration of PA to increase muscle protein synthesis. As stated above, because of the well known gastro-intestinal degradation and entry into the phospholipid synthetic cycle upon uptake into the vascular system, only actual in vivo experimentation can resolve this question. Previous to the present invention, oral administration of PA has never been studied. Muscle growth is very complex, with many factors contributing to the optimal compositions and methods for promoting growth. In addition to the signaling at the gene level as discussed above, good muscle health begins with adequate nutrition. The diet can be optimized to provide the best combination of nutrients for each individual. Supplements are available to increase the intake of the carbohydrates, proteins and fats. For example, whey protein is a complete protein, containing the proper balance of essential amino acids and is easily digested. Partially hydrolyzed collagen is another complete protein and is even more easily digested. An athlete in the muscle building phase can take 20 to 100 grams of protein daily. Protein supplement of an easily digestible protein such as whey or collagen is even more beneficial for the aging, cachectic or bedridden person.

Recent emphasis on the α-lipoic acids has indicated an additional benefit. Some herbal products such as Russian tarragon, *Cissus quadruangularis* or *Gymnema sylvestre* can be beneficial. Others include amino acids, creatine, L-carnatine, glycine propyline-L-carnatine, bitter melon, *cissus quadruangularis*, cinnamon and fenugreek, creatinol-o-phosphate, leucine peptide, leucine, CLA, tribulus, ribose, caffeine, beta alanine, ZMA, betaine, L-aspartic acid and carnosine, alone or in combination. Each of these supplements, acting at a different level of metabolism, can enhance the effect of PA-enriched lecithin administration.

Prime among them the recommended nutritional supplements, creatine is phosphorylated by creatine kinase (CK) to form an energy reservoir, especially in muscle tissue, for the resynthesis of ATP expended during exercise. Numerous studies have shown that an increase in intramuscular creatine levels with creatine supplementation is variable, with mammals falling into the "responder" or "nonresponder" groups. It is hypothesized that much of this variability lies within the regulation and activity of the creatine transporter. In one study the observation was that approximately 20 to 30% of participants following a creatine loading regime did not respond with an increase in intracellular creatine (Greenhaff et al. 1994 Amer. J. Physiol. 266 (5Pt 1):E725-30). Another study conducted a descriptive profile of the characteristics of individuals portraying Greenhaff's classification of responders versus nonresponders (Syrotuik et al 2004). Since mTOR has been shown to stimulate the creatine transporter SLC6A8 through mechanisms at least partially shared by the serum and glucocorticoid-induced kinase SGK1 (Shojaiefard et al 2006) it is hypothesized that creatine supplementation combined with PA may show a synergistic effect, not only in extending the benefits of creatine supplementation to creatine non-responders, but also to increase the creatine effect in responders. Therefore a composition of creatine with PA or PA-enriched lecithin is recommended. Creatine is available in several forms such as creatine salt, creatine ester, creatine ether, creatinol, creatinol ether, creatinol salt, all of which are included within the scope of the appended claims.

Beyond nutritional supplements, hormones such as testosterone, human growth hormone, insulin and insulin-like growth hormones can also play a role in promoting anabolism. These hormones may be especially efficacious for cachectic patients. Other "micronutrients" such as chromium, vanadium and Coenzyme Q10 may be added to the diet.

It can be concluded that signaling through mTOR is necessary for mechanically induced growth of skeletal muscle and that mTOR signaling requires a certain concentration of PA. Until this invention was made, it was unknown whether PA could be sufficiently raised by ingestion by an intact mammal to affect and significantly amplify the growth signaling cascade. Surprisingly, it has been found that PA amplifies the growth signaling cascade, even in the absence of mechanical induction. Thus, PA is important in shifting the metabolism from the catabolic state to the anabolic state and improving nitrogen balance.

The following experiments were carried out to show more clearly the effect of PA administration in increasing muscle hypertrophy and strength. These examples are given in detail in order to more clearly explain how to make and use the invention and do not limit the scope of the appended claims. The exemplar subject is human, but the results are readily obtained with other mammals such as the horse and the dog, with adjustments in dosage appropriate to body size. Those with skill in the art can readily make minor changes or variations without departing from the scope of the claims.

Example 1. Enrollment Criteria

A double-blinded study was planned to test the effect of PA on muscle strength. The inclusion criteria were: participation in a resistance training program on a regular basis at recreational level or higher; no physical limitations as determined by health and activity questionnaire; between the ages of 18 and 29. Subjects were excluded if they had allergy to soy, dairy, egg and wheat ingredients, peanuts, seeds and tree nuts. Those taking any other nutritional supplement or performance enhancing drug were excluded. Finally, subjects were excluded if it was determined they were unable or unwilling to perform the physical exercise to be performed for the study.

Example 2. Recommended Supplements

Essentially pure PA and PA-enriched lecithin enriched lecithin are prepared from soy lecithin by enzymatic conversion. The product produced by Chemi Nutra, Inc. (White Bear Lake, Minn.) contains 50-60% phosphatidic acid, 5-15% phosphatidylcholine, 1-5% lyso-phosphatidylcholine and 1-5% N-acyl phosphatidyl ethanolamine. The PA-enriched lecithin was given in four 400 milligram capsules to provide 1.6 grams of PA-enriched lecithin. The placebo was rice flour in a capsule identical in weight and color to the PA-enriched lecithin capsule.

The method as described below includes a protein snack. Any easily digested protein may be given. The preferred protein is partially hydrolyzed and termed "collagen protein" with the following composition. Note that proline and hydroxylproline comprise about a quarter of the amino acids and leucine content is low. This protein was chosen because leucine can have an effect on muscle and for clarity, that effect was minimized by choice of protein.

TABLE I

| Amino Acid (AA) | g AA/100 g product |
| --- | --- |
| Alanine | 7.6 |
| Arginine | 7.8 |
| Aspartic Acid | 5.1 |
| Cystine | 0.0 |
| Glutamic Acid | 10.5 |
| Glycine | 18.2 |
| Histidine | 1.2 |
| Hydroxylysine | 0.5 |
| Hydroxylproline | 10.8 |
| Isoleucine | 1.4 |
| Leucine | 2.8 |
| Lysine | 3.1 |

TABLE I-continued

| Amino Acid (AA) | g AA/100 g product |
| --- | --- |
| Methionine | 0.6 |
| Phenylalanine | 1.9 |
| Proline | 12.2 |
| Serine | 2.8 |
| Threonine | 1.7 |
| Tryptophan | 0.0 |
| Tyrosine | 0.6 |
| Valine | 2.0 |

Example 3. Resistance Training Schedule

Four recreationally trained, young, healthy men, with at least one year of resistance training experience who met the enrollment criteria, were recruited for this study. All subjects performed the same training program, four days each week, split routine program as described below in Table II. The four-day a week workout that was recommended to each subject included core exercises (denoted with an asterisk) which were a requirement of the study. Other exercises, assistance exercises, could be substituted for the core exercises only with the investigator's approval. However, all sets and repetitions were required to be the same. Subjects were allowed a 90 second rest period between each set. No additional sets or exercises were allowed as this would change the training volume, defined as the total work load (reps times weight).

TABLE II

Eight Week Resistance Training Program

| Exercise | Sets/Reps (RM) |
| --- | --- |
| Monday/Thursday | |
| Bench Press* | 1.4 × 10 to 12 |
| Incline Dumbbell Press | 3 × 10 to 12 |
| Seated Shoulder Press* | 1.4 × 10 to 12 |
| Upright Rows | 3 × 10 to 12 |
| Lateral Raises | 3 × 10 to 12 |
| Shrugs | 3 × 10 to 12 |
| Triceps Pushdown | 3 × 10 to 12 |
| Triceps Extension | 3 × 10 to 12 |
| Situps | 3 × 25 |
| Tuesday/Friday | |
| Squats* | 1.4 × 10 to 12 |
| Lunge/Front Squat | 3 × 10 to 12 |
| Leg Curl | 3 × 10 to 12 |
| Knee Extension | 3 × 10 to 12 |
| Calf Raises | 3 × 10 to 12 |
| Lat Pulldown | 4 × 10 to 12 |
| Seated Row | 4 × 10 to 12 |
| EZ Bar Curl | 3 × 10-12 |
| Dumbbell Curls | 3 × 10 to 12 |
| Situps | 3 × 25 |

*denotes required exercise

The subjects were randomly divided into two groups. The test group received 4 capsules of 400 mg equaling 1.6 grams per day of PA-enriched lecithin (Mediator®, Chemi Nutra, Inc., White Bear Lake, Minn.). The control subjects received 4 capsules of 400 mg equaling 1.6 grams per day of rice flour. Subjects consumed either the test supplement or the placebo 15 minutes prior to workout. At the end of each workout, subjects were provided with a collagen protein drink consisting of 36 grams of collagen peptides mixed with 500 ml of water. On days of no workout, subjects consumed the respective capsules at approximately the same time of day that they worked out. During these non-workout days, subjects did not receive the protein drink.

At weeks 1 and 7 (pre- and post-study) subjects performed a 1-repetition maximum (1RM) strength test on the squat and bench press exercises. Each subject performed a warm-up set using a resistance that is approximately 40-60% of his perceived maximum and then performed three to four subsequent attempts to determine the 1RM. Subjects were allowed 3 to 5 minutes of rest between each lift. Results are summarized in Table III.

TABLE III

| Strength (1RM) Bench Press | | | | | | | |
|---|---|---|---|---|---|---|---|
| PA: average increase: +20 kg (plus 10.5% | | | | Placebo: unchanged (0%) | | | |
| | Pre | Post | Delta | | Pre | Post | Delta |
| Subject 1 | 225 kg | 250 kg | +25 kg | Subject 3 | 220 kg | 220 kg | 0 |
| subject 2 | 155 kg | 170 kg | +15 kg | Subject 4 | 175 kg | 175 kg | 0 |
| Strength (1RM) Squat | | | | | | | |
| PA: Average increase: +40 kg (+21%) | | | | Placebo: unchanged +2.5 kg (+1%) | | | |
| | Pre | Post | Delta | | Pre | Post | Delta |
| Subject 1 | 225 kg | 285 kg | +60 kg | Subject 3 | 290 kg | 290 kg | 0 |
| Subject 2 | 155 kg | 175 kg | +20 kg | Subject 4 | 215 kg | 220 kg | 0 |

PA supplementation resulted in an increase in strength in the bench press of 10.5% and in the squat of 21%. Supplementation with the placebo resulted in no increase in strength in either exercise.

The effects of PA supplementation on muscle mass and training volume were determined in 2 recreationally trained, young, healthy men, with at least one year of resistance training experience. As above, these subjects received either 1.6 grams per day of Mediator® (Chemi Nutra, White Bear Lake, Minn.) or 1.6 grams of rice flour for 6 weeks. Changes in muscle mass were measured by analyzing the muscle thickness of the vastus lateralis, the large lateral muscle on the thigh, using a GE Logiq PS Premium BT09 (Wauwatosa, Wis.). Training volume was calculated as weight lifted times repetitions performed.

The two subjects performed the same 6-week training program, consisting of a 2 day per week lower body resistance program (squats, lunge/front squat, leg curl, knee extension, calf raises, seated row, EZ bar curls, dumbbell curls.) There was a 90 second rest period between each set. The addition of any additional sets or exercises was prohibited as it would change the training volume.

PA supplementation resulted in an increase of 13% in training volume (pre: 49,640; post: 56,000), whereas placebo had no effect on training volume (pre: 92,800; {post: 92,800). PA supplementation resulted in an increase in muscle thickness of 17.0% (pre: 2.24 cm; post: 2.62 cm), whereas training with placebo resulted in an increase of muscle thickness of 15.6% (pre: 2.57 cm; post: 2.97 cm). In summary, PA supplementation resulted in greater increase in muscle mass, as demonstrated in this study, resulting in an increase of 9.0% more between a PA supplemented subject and a non-supplemented subject. In addition, PA supplementation resulted in greater increase in training volumes.

Example 4. Creatine Responder

As discussed above, creatine is a known muscle building substance, but about 30% of any population do not respond to creatine administration.

A. RJ, a 42-year old male, 198 cm tall, a known non-responder to creatine supplementation, followed a two-week strength training program while testing whether supplementation with PA-enriched-lecithin improves creatine response. Total starting total body weight and strength were measured on day one, followed by the training program, consisting of concentric and eccentric isotonic lifting exercises that worked the upper and lower body muscle groups. Either free weights or weight machines were used once or twice weekly. Strength training was performed three times per week with at least one day of rest between sessions, which alternated between lower and upper body exercises. During the two-week period, a total of six training sessions (three upper and three lower) were performed. Each exercise included two sets of ten repetitions at 30% and 60% 1RM, followed by two sets of 3 to 5 repetitions at 90% 1RM.

The lower body exercise included seven different exercises: seated leg press, leg curls, standing calf raises, leg extensions, inclined leg lift, inverted situps (back extension) and 45° inclined situps. The upper body exercise consisted of seven different exercises: bench press, latissimus pulldown, triceps pulldown, inclined dumbbell curls, seated preacher curls, seated rows, and CyBec Pec Fly.

Total upper and lower body weight lifted were calculated as the average weight lifted during the last three sets multiplied by the average repetition in each set. Total strength was determined as the combined lower and upper total weight lifted. Total body weight was determined after day 8 and day 15. Strength was measured on days 1 and 15.

A four-week rest period followed the first two-week training program. The same program was repeated twice, the control was supplementation of creatine monohydrate (Creapure, Alzchem, Germany) 4 times 5 grams per day for five days of loading, followed by nine days of five grams creatine monohydrate. During the second program, creatine monohydrate was given as for the control program with the addition of PA-enriched lecithin (Chemi Nutra, White Bear Lake, Minn.) which was about 50% PA. The results are shown in Table IV.

TABLE IV

| Day | No Supplement | Creatine Supplement | Creatine plus PA-enriched Lecithin |
|---|---|---|---|
| 1: weight, kg | 90.0 | 88.8 | 88.5 |
| 8: weight, kg | 88.6 | 88.3 | 89.7 |
| 15: weight, kg | 88.2 | 88.0 | 90.1 |

As can be noted, creatine loading alone was not effective in preventing a slight weight loss, while creatine plus PA-enriched lecithin reversed the weight loss and allowed a slight weight gain, presumably due to an increased muscular creatine concentration with concomitant muscle weight gain, as expected from the known non-responder status of RJ. Looking at total strength substantiated this theory: during the two-week baseline period, strength increased 6%, the same as during the creatine supplement period, which showed a similar, 5% strength increase, verifying that RJ was a creatine non-responder. The supplementation with both creatine and PA-enriched lecithin showed a gain in strength of 13.4%, more than double that of exercise alone or supplementation with creatine plus exercise.

B. MP, a 43-year old male, 185 cm tall, also a known non-responder to creatine supplementation, followed a three-week strength training program while testing whether supplementation with PA-enriched-lecithin improves creatine response. Total starting total body weight and strength were measured on day one, followed by the training program, consisting of concentric and eccentric isotonic lifting exercises that worked the upper and lower body muscle groups with either free weights or weight machines used once or twice weekly. Strength training was performed three times per week with at least one day of rest between sessions, which alternated between lower and upper body exercises. During the three-week period, a total of 10 training sessions (five upper body and five lower body) were performed. Each exercise included two sets of ten repetitions at 40% and 65% 1RM, followed by two sets of 3 to 5 repetitions at 90% 1RM.

The lower body exercise included seven different exercises: seated leg press, leg curls, standing calf raises, leg extension, inclined leg lift, inverted situps (back extension) and 45° inclined situps. The upper body exercise consisted of seven different exercises: bench press, latissimus pull-down, triceps pulldown, inclined dumbbell curls, seated preacher curls, seated rows, and CyBec Pec Fly. Total upper and lower body weight lifted were calculated as the average weight lifted during the last three sets multiplied by the average repetition in each set. Total strength was determined as the combined lower and upper total weight lifted. Total body weight was determined after day 8 and day 22. Strength was measured on days 1 and 22.

A four-week rest period followed the first three-week training program. The same program was repeated twice, the control was supplemented with creatine monohydrate (Creapure®, Alzchem, Germany) 5 grams per day of five grams creatine monohydrate for 21 days. During the second program, creatine monohydrate was given as for the control program with the addition of 1 gram per day PA-enriched lecithin (Chemi Nutra, White Bear Lake, Minn.) which was about 50% PA. The results are shown in Table V.

TABLE V

| Day | No Supplement | Creatine Supplement | Creatine plus PA-enriched Lecithin |
|---|---|---|---|
| 1: weight, kg | 82.0 | 81.9 | 81.5 |
| 10: weight, kg | 81.8 | 81.5 | 82.9 |
| 22: weight, kg | 81.7 | 81.2 | 83.1 |

As can be noted, creatine loading alone was not effective in preventing a slight weight loss, while creatine plus PA-enriched lecithin reversed the weight loss and allowed a slight weight gain, presumably due to an increased muscular creatine concentration with concomitant muscle weight gain, as expected from the known non-responder status of RJ. Looking at total strength substantiated this theory: during the two-week baseline period, strength increased 5%, the same as during the creatine supplement period, which showed a similar, 5% strength increase, verifying that RJ was a creatine non-responder. The supplementation with both creatine and PA-enriched lecithin showed a gain in strength of 11.5%, more than double that of exercise alone or supplementation with creatine plus exercise.

Example 5. PA-Enriched Lecithin for the Improvement of Nitrogen Balance

Preliminary studies show that those unable to exercise, such as the bedridden or patients with diseases causing cachexia, can improve their condition with a shift of metabolism from catabolic to anabolic. The primary aspect of cachexia is the loss of protein from muscle breakdown. Since about 60% to 70% of bodily protein is found in muscle and the nitrogen is excreted as urea, measurement of 24-hour urea outcome versus protein nitrogen intake gives the nitrogen balance. When the excretion of nitrogen is greater than the ingestion of protein nitrogen, the patient is said to be in negative nitrogen balance leading to sarcopenia. There are several ways of determining nitrogen balance. First, a diary of foods eaten can be kept and protein intake recorded and compared with a 24 hour collection of urinary nitrogen. This direct measurement is often standard care in hospitals and nursing homes for these patients.

Another indicium is 24 hour urinary creatinine. Creatinine is the metabolite of creatine, as noted above, an important compound in muscle. Creatinine is excreted without reabsorption from the kidney tubules and can be determined as an estimate of renal function. Creatinine recovery varies greatly from patient to patient and is affected by such things as degree of hydration. However, when a baseline is established, variations from the patient's idiosyncratic "normal" creatinine excretion is indicative of muscle breakdown and is a secondary indicium of nitrogen balance.

The patients will be given 0.5 to four grams of PA-enriched lecithin three times a day. While oral administration is preferred, for those patients unable to ingest or who are on intravenous or intraarterial therapies, PA or PA-enriched lecithin may be infused. The results will show an improvement in nitrogen balance.

Example 6. Increase of Muscle Mass and Strength in the Elderly

Even healthy older subjects may lose muscle to the point of sarcopenia. It may be considered inevitable and irreversible. However, it has been shown that 70-year old adults show a response to the known muscle stimulant β-hydroxy-β-methyl butyrate similar to that of young adults. (Vukovich, et al. 2001 Am. Soc. Nutr. Sci. 2049-2053). Therefore, the compositions and methods of this invention will improve the muscle mass and strength of older subjects. It is especially recommended to combine ingestion of about 5 grams of creatine and 3 grams of creatine 1 to 3 times daily in their exercise regimen.

All references cited herein are incorporated in their entirety.

We claim:

1. A method of increasing muscle mass and strength in a subject, the method consisting of orally administering to a healthy exercising subject a therapeutically effective dose consisting of phosphatidic acid in the absence of creatine, wherein the therapeutically effective dose is 0.1 grams to 40 grams, and wherein the muscle strength of the subject increases by at least 10% after six weeks of resistance training, compared to the muscle strength of a similarly trained subject that does not ingest the effective dose of phosphatidic acid.

2. A method of increasing muscle mass and strength in a subject, the method consisting of
   orally administering to a healthy exercising subject a therapeutically effective dose consisting of phosphatidic acid in the absence of creatine, wherein the therapeutically effective dose is 0.1 grams to 40 grams, wherein the muscle strength of the subject increases by at least 10% after six weeks of resistance training, compared to the muscle strength of a similarly trained subject that does not ingest the effective dose of phosphatidic acid, and
   orally administering to said healthy subject 20 grams to about 100 grams of collagen protein after exercise.

3. The method of claim 2 wherein the effective dose of phosphatidic acid is about 800 mg per day.

4. The method of claim 1, wherein the effective dose of phosphatidic acid is about 800 mg per day.

* * * * *